United States Patent [19]

Albrecht et al.

[11] Patent Number: 5,329,002

[45] Date of Patent: Jul. 12, 1994

[54] ANTIBACTERIAL CEPHALOSPORIN COMPOUNDS

[75] Inventors: Harry A. Albrecht, Towaco; Dennis D. Keith, Montclair; Chung-Chen Wei, Cedar Knolls; Manfred Weigele, North Caldwell; Roxana Yang, West Caldwell, all of N.J.

[73] Assignee: Hoffmann-La Roche Inc., Nutley, N.J.

[21] Appl. No.: 549,674

[22] Filed: Jul. 6, 1990

Related U.S. Application Data

[63] Continuation of Ser. No. 197,944, May 24, 1988, abandoned, which is a continuation-in-part of Ser. No. 175,471, Mar. 31, 1988, abandoned.

[51] Int. Cl.$^5$ .................. C07D 501/14; A61K 31/545
[52] U.S. Cl. ..................................... 540/222; 540/221
[58] Field of Search ................. 540/221, 222; 514/202

[56] References Cited

U.S. PATENT DOCUMENTS

| Re. 32,491 | 9/1987 | Iwanami et al. |
|---|---|---|
| 3,971,778 | 7/1976 | Cook et al. |
| 4,152,432 | 5/1979 | Heymes et al. |
| 4,263,432 | 4/1981 | Iwanami et al. |
| 4,292,317 | 9/1981 | Pesson |
| 4,399,131 | 8/1983 | Dürckheimer |
| 4,404,373 | 9/1983 | Iwanami et al. |
| 4,468,394 | 8/1984 | Machida et al. |
| 4,476,123 | 10/1984 | Labeeuw et al. |
| 4,501,743 | 2/1985 | Breuer et al. |
| 4,581,352 | 4/1986 | Foster et al. |
| 4,604,387 | 8/1986 | Labeeuw et al. |
| 4,608,373 | 8/1986 | Shibanuma et al. |
| 4,634,697 | 1/1987 | Hamashima |
| 4,656,166 | 4/1987 | Salhi et al. |
| 4,670,444 | 6/1987 | Grohe et al. |

(List continued on next page.)

FOREIGN PATENT DOCUMENTS 060745 9/1982 European Pat. Off.

(List continued on next page.)

OTHER PUBLICATIONS

Gary Weiss, Barron's, Mar. 10, 1986, pp. 34–64.
(List continued on next page.)

*Primary Examiner*—Nicholas S. Rizzo
*Attorney, Agent, or Firm*—George M. Gould; George W. Johnston; Alan P. Kass

[57] ABSTRACT

There are presented antibacterial cephalosporins having broad antimicrobial activity as well as intermediates for their formation, such compounds having the formula

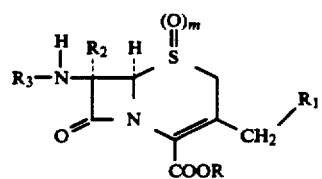

wherein R is hydrogen or a carboxylic acid-protecting group; $R_1$ is a substituted piperazinium group of the formula

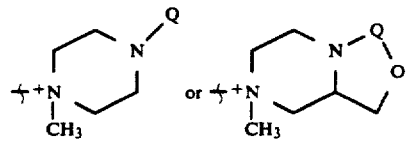

in which Q represents a substituted quinolinyl or naphthyridinyl group and the piperazine nucleus may be optionally substituted with one or more lower alkyl groups; $R_2$ is selected from the group consisting of hydrogen, lower alkoxy, lower alkylthio and amido; $R_3$ is hydrogen or an acyl group; and m is 0, 1 or 2, preferably 0;

as well as the corresponding readily hydrolyzable esters, pharmaceutically acceptable salts and hydrates of these compounds.

29 Claims, No Drawings

U.S. PATENT DOCUMENTS

| | | |
|---|---|---|
| 4,753,925 | 6/1988 | Grohe et al. |
| 4,753,953 | 6/1988 | Masuzawa et al. |
| 4,758,567 | 6/1988 | Desideri et al. |
| 4,762,831 | 8/1988 | Grohe et al. |
| 4,762,845 | 8/1988 | Chu et al. |
| 4,767,762 | 8/1988 | Chu |
| 4,808,711 | 2/1989 | Shimizu et al. |
| 4,844,902 | 7/1989 | Grohe |
| 4,946,837 | 8/1990 | Miyoke et al. |
| 4,946,847 | 8/1990 | Jolidon et al. |
| 5,089,491 | 7/1990 | Albrecht et al. .............. 514/206 |

FOREIGN PATENT DOCUMENTS

| | | |
|---|---|---|
| 160546 | 6/1985 | European Pat. Off. |
| 187456 | 11/1985 | European Pat. Off. |
| 178980 | 4/1986 | European Pat. Off. |
| 366189 | 5/1990 | European Pat. Off. |
| 366193 | 5/1990 | European Pat. Off. |
| 366640 | 5/1990 | European Pat. Off. |
| 366641 | 5/1990 | European Pat. Off. |
| 366643 | 5/1990 | European Pat. Off. |
| 1591439 | 6/1981 | United Kingdom |
| 87/05297 | 9/1987 | World Int. Prop. O. |

OTHER PUBLICATIONS

Journal of Bacteriology, vol. 110, No. 3, pp. 988–991 (1972).
Antimicrobial Agents and Chemotherapy, vol. 10, No. 2, pp. 245–249 (1976).
Biochem. J., 116, 371 (1970).
Progress in Drug Research, 21, 9, 9 (1977).
The Chemistry and Biology of β-Lactam Antibiotics, vol. 3, App. A pp. 379–392 (1982).
Antimicrobial Agents and Chemotherapy, 28(4), 581 (1985).
Agnew. Chem. Int. Ed. Engl., 24, 180 (1985).
Annual Reports in Medicinal Chemistry, 20, 145 (1985).
Annual Reports in Medicinal Chemistry, 21, 139 (1986).
Antimicrobial Agents and Chemotherapy, 31(4), 614 (1987).
American Journal of Medicine, 82, (Supp. 4A), 12 (Apr. 27, 1989).
J. Antimicrobial Chemotherapy, 17, 5 (1986).
Annual Reports in Medicinal Chemistry, 21, 117 (1987).
Antimicrobial Agents and Chemotherapy, 31(11) 1831 (1987).
Drugs, 34 (Supp. 2), 1 (1987).
J. Med. Chem., 31, 983 and 991 (1988).
Hackh's Chemical Dictionary, Grant, J., ed., 3rd Ed., McGraw-Hill, New York, p. 814 (1944).
*J. Med. Chem.*, 5, 1063 (1962).
*J. Med. Chem.*, 20(6), 791 (1977).
*J. Med. Chem.*, 21(5), 485 (1978).
*J. Med. Chem.*, 23(12), 1358 (1977).
*J. Med. Chem.*, 27(3), 292 (1984).
*J. Med. Chem.*, 27(9), 1103 (1984).
*J. Med. Chem.*, 27(12), 1543 (1984).
*J. Med. Chem.*, 28(11), 1558 (1985).
*J. Med. Chem.*, 29(3), 394 (1986).
*J. Med. Chem.*, 29(4), 445 (1986).
*J. Med. Chem.*, 30(3), 504 (1987).
*Tetrahedron*, 23, 4719 (1967).
*Synthesis*, 787 (1979).
*J. Heterocyclic Chem.*, 22, 1033 (1985).
O'Callaghan, C. H., et al., Antimicrobial Agents and Chemotherapy, 10, No.2, 245–248 (1976).
Derwent Abstract No. 85-278057 of JA Application No. 60-228,487 Nov. 13, 1985.

ANTIBACTERIAL CEPHALOSPORIN COMPOUNDS

CROSS REFERENCE TO RELATED APPLICATION

This invention is a continuation of application Ser. No. 07/197,944, filed May 24, 1988, now abandoned, which is a continuation-in-part of application Ser. No. 07/175,471, filed Mar. 31, 1988, now abandoned.

DESCRIPTION OF THE INVENTION

The present invention relates to intermediates and antibacterial compounds of the formula

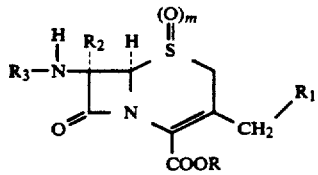

wherein R is hydrogen or a carboxylic acid-protecting group; $R_1$ is a substituted piperazinium group of the formula

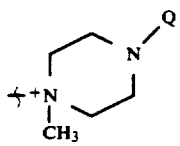

in which Q represents a substituted quinolinyl or naphthyridinyl group and the piperazine nucleus may optionally be substituted with one or more lower alkyl groups: $R_2$ is selected from the group consisting of hydrogen, lower alkoxy, lower alkylthio and amido; R is hydrogen or an acyl group: and m is 0, 1 or 2, but preferably 0; as well as the corresponding readily hydrolyzable esters, pharmaceutically acceptable salts and hydrates of these compounds.

As used herein, the terms "lower alkyl" and "alkyl" refer to both straight and branched chain saturated hydrocarbon groups having 1 to 8, and preferably 1 to 4, carbon atoms, for example, methyl, ethyl, propyl, isopropyl, tertiary butyl, and the like.

As used herein, the term "lower alkoxy" refers to a straight or branched chain hydrocarbonoxy group wherein the "alkyl" portion is a lower alkyl group as defined above. Examples include methoxy, ethoxy, propoxy and the like.

The term "halogen", or "halo", used herein refers to all four forms, that is, chloro, bromo, iodo and fluoro, unless specified otherwise.

The term "acyl" used in conjunction with $R_3$ herein refers to all organic radicals derived from an organic carboxylic acid by removal of the hydroxyl group. Although the group $R_3$ may be any one of many acyl radicals, certain acyl groups are preferred, as described below.

Exemplary acyl groups are those groups which have been used in the past to acylate beta-lactam antibiotics. including 6-aminopenicillanic acid and derivatives and 7-aminocephalosporanic acid and derivatives: see, for example. *Cephalosporins and Penicillins* edited by Flynn, Academic Press (1972), Belgian patent 866,038, published Oct. 17, 1978, Belgian patent 867,994, published Dec. 11, 1978, U.S. Pat. No. 4,152,432, issued May 1, 1979, U.S. Pat. No. 3,971,778, issued Jul. 27, 1976, and U.S. Pat. No. 4,173,199, issued Oct. 23, 1979. The portions of these references describing various acyl groups are incorporated herein by reference. The following list of acyl groups is presented to further exemplify the term "acyl", without intending to limit that term to only those groups set forth:

(a) Aliphatic acyl groups having the formula

wherein $R_5$ is hydrogen, alkyl, cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Aromatic acyl groups having the formula

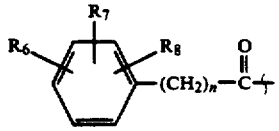

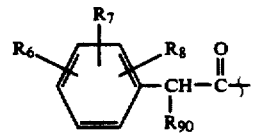

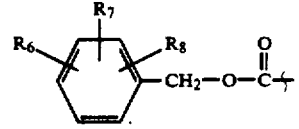

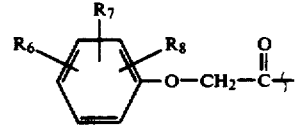

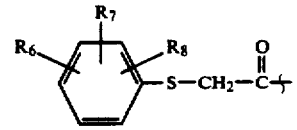

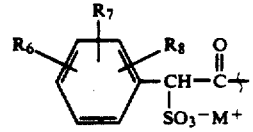

and

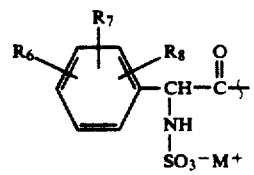

wherein n is 0, 1, 2 or 3; $R_6$, $R_7$, and $R_8$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R_{90}$ is amino, acylamino, hydroxyl, a carboxyl salt, protected carboxy such as benzyloxycarbonyl, formyloxy or azido.

Preferred aromatic acyl groups include those having the formula

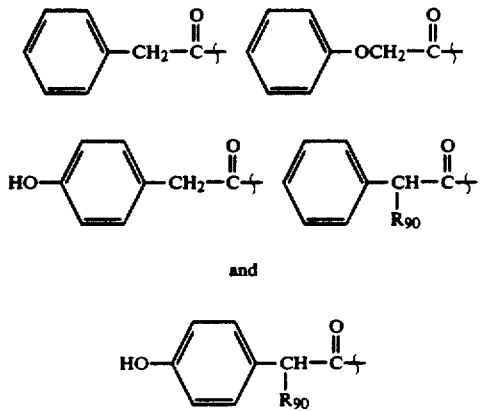

and

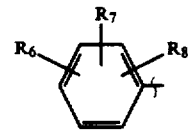

$R_{90}$ is preferably an amino group, a hydroxy group, or a carboxyl salt or sulfo salt.

Examples of the other aromatic acyl groups suitable for the purposes of the present invention are sulfophenylacetyl, hydroxy- sulfonyloxyphenylacetyl, sulfamoylphenylacetyl, (phenoxy- carbonyl)phenylacetyl, (p-tolyloxycarbonyl)phenylacetyl, formyloxyphenylacetyl, carboxyphenylacetyl, formylamino- phenylacetyl, benzyloxycarbonylphenylacetyl, 2-(N,N-dimethylsulfamoyl)-2-phenylacetyl, etc.

(c) Heteroaromatic acyl groups having the formula

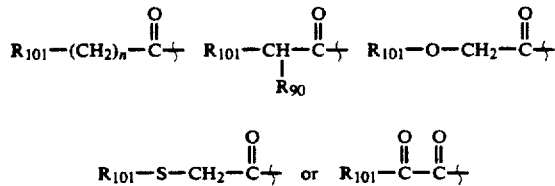

wherein n is 0, 1, 2 or 3; $R_{90}$ is as defined above; and $R_{101}$ is a substituted or unsubstituted 5-, 6- or 7-membered heterocyclic ring containing 1, 2, 3 or 4 (preferably 1 or 2) hereto atoms selected from among nitrogen, oxygen and sulfur. Exemplary heterocyclic rings are thienyl, furyl, pyrrolyl, pyridinyl, pyrazinyl, thiazolyl, pyrimidinyl and tetrazolyl Exemplary substituents are halogen, hydroxyl, nitro, amino, cyano, trifluoromethyl, alkyl of 1 to 4 carbon atoms, or alkoxy of 1 to 4 carbon atoms.

Preferred heteroaromatic acyl groups include those groups of the above formulas wherein $R_{101}$ is 2-amino-4-thiazolyl, 2-amino-5-halo-4-thiazolyl, 4-aminopyridin-2-yl, 2-amino-1,3,4-thiadiazol-5-yl, 2-thienyl, 2-furanyl, 4-pyridinyl or 2,6-dichloro-4-pyridinyl.

(d) [[(4-Substituted-2,3-dioxo-1-piperazinyl)carbonyl]amino]acetyl groups having the formula

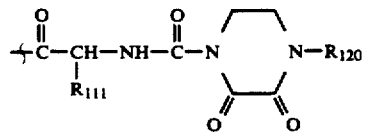

wherein $R_{111}$ is alkyl, hydroxyalkyl or an aromatic heterocyclic or carboxylic group, such as those of the formula

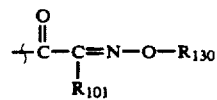

wherein $R_6$, $R_7$ and $R_8$ are as previously defined or heteroaromatics as included within the definition of $R_{101}$; and $R_{120}$ is alkyl, substituted alkyl (wherein the alkyl group is substituted with one or more halogen, cyano, nitro, amino or mercapto groups), e.g., 4-lower alkyl (preferably ethyl or methyl)-2.3-dioxo-1-piperazinecarbonyl-D-phenylglycyl.

(e) (Substituted oxyimino) arylacetyl groups having the formula

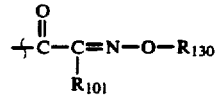

wherein $R_{101}$ is as defined above and $R_{130}$ is hydrogen, lower alkyl and $C_3$-$C_7$ cycloalkyl or substituted lower alkyl wherein the alkyl group is substituted with one or more halogen, cyano, nitro, amino, mercapto, lower alkylthio, aromatic group (as defined by $R_{111}$), carboxyl (including salts thereof), amido, carbamoyl, lower alkoxycarbonyl, phenylmethoxycarbonyl, diphenylmethoxycarbonyl, hydroxyalkoxyphosphinyl, dihydroxyphosphinyl, hydroxy(phenylmethoxy)phosphinyl, di-lower alkoxyphosphinyl substituents, carboxyl lower alkyl or carboxyl-$C_3$-$C_7$-cycloalkyl.

Examples of the

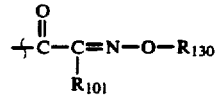

grouping are [2-[(chloroacetyl)amino]-4-thiazolyl](methoxyamino)acetyl, (2-amino-4-thiazolyl)(1-methylethoxyimino)acetyl, (2-amino-4-thiazolyl)(methoxyimino)acetyl, (2-furyl)(methoxyimino)acetyl, (4-hydroxyphenyl)(methoxyimino)acetyl, (methoxyimino)(phenyl)acetyl, (hydroxyimino)(phenyl)acetyl, (hydroxyimino)(2-thienyl)acetyl, [[(dichloroacetyl)oxy]imino](2-thienyl)acetyl, [5-chloro-2-[(chloroacetyl)amino]-4-thiazolyl](methoxyimino)acetyl, (2-amino-5-chloro-4-thiazolyl)(methoxyimino)acetyl, [[[1-(1,1-dimethylethoxy)carbonyl]-1-methylethoxy]imino]-2-sulfoamino-4-thiazolyl)acetyl, [[[1-(1,1-dimethylethoxycarbonyl]-1-methylethoxy]imino]][2-(triphenylmethyl)amino]-4-thiazolyl]acetyl, (methoxyimino)(2-sulfoamino-4-thiazolyl)acetyl, [(1-methylethoxy)imino][2-[(methylsulfonyl)amino]-4-thiazolyl]acetyl, [(3-methylsulfonyl)-[3H]-thiazolimin-4-yl]-[1-(methylethoxy)imino]acetyl, [[2-(chloracetyl)amino]-4-thiazolyl]][[[[(4-nitrophenyl)-methoxy]carbonyl]methoxy]imino]acetyl, (2-amino-4-thiazolyl)[(carboxymethoxy)imino]acetyl, (2-amino-4-thiazolyl)[1-carboxy-(1-methylethoxy)imino]acetyl, (2-amino-4-thiazolyl)[-[(aminocarbonyl)methoxy]imino]acetyl.

(f) (Acylamino) acetyl groups having the formula

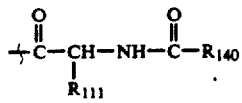

wherein $R_{111}$ is as defined above and $R_{140}$ is

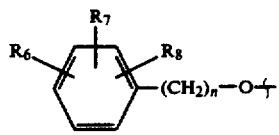

(where $R_6$, $R_7$, $R_8$ and n are as previously defined), hydrogen, lower alkyl, substituted lower alkyl, amino, alkylamino, dialkylamino, (cyanoalkyl)amino, hydrazino, alkyl hydrazino, aryl hydrazino or acyl hydrazino.

Preferred (acylamino)acetyl groups of the above formula include those groups wherein $R_{140}$ is amino, or acylamino. Also preferred are those groups wherein $R_{111}$ is phenyl or 2-thienyl.

(g) Substituted oxyimino acetyl groups having the formula

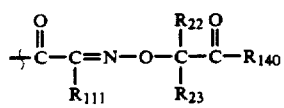

wherein $R_{111}$ and $R_{140}$ are as defined above, and $R_{22}$ and $R_{23}$ are independently selected from the group consisting of hydrogen and lower alkyl, or $R_{22}$ and $R_{23}$ taken together with the carbon atom to which they are attached form a $C_3$-$C_7$ carboxylic ring, for example, cyclopropyl, cyclobutyl or cyclopentyl.

Preferred substituted oxyimino acetyl groups of the above formula include those groups wherein $R_{140}$ is hydroxy or amino. Also preferred are those groups wherein $R_{111}$ is 2-amino-4-thiazolyl.

(h) [[[3-Substituted-2-oxo-1-imidazolidinyl]carbonyl]amino]acetyl groups having the formula

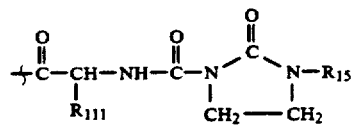

wherein $R_{111}$ is as defined above and $R_{15}$ is hydrogen, alkylsulfonyl, arylmethyleneamino (i.e., O—N=CHR$_{111}$ wherein $R_{111}$ is as defined above), $CR_{16}$ (wherein $R_{16}$ is hydrogen, alkyl or halogen substituted alkyl), aromatic group (as defined by $R_{111}$ above), alkyl or substituted alkyl (wherein the alkyl group is substituted with one or more halogen, cyano, nitro, amino or mercapto groups).

Preferred [[[3-substituted-2-oxo-1-imidazolidinyl]carbonyl]amino]acetyl groups of the above formula include those wherein $R_{111}$ is phenyl or 2-thienyl. Also preferred are those groups wherein $R_{15}$ is hydrogen, methylsulfonyl, phenylmethyleneamino or 2-furylmethyleneamino.

As used herein the substituted piperazinium substituent $R_1$ includes, among others, compounds of the formulae:

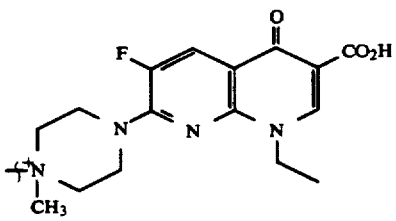

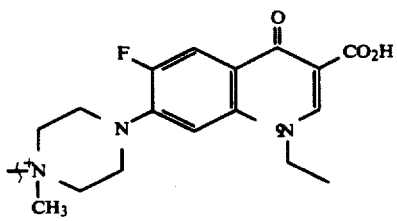

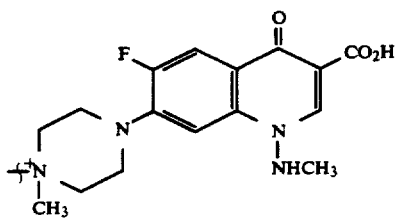

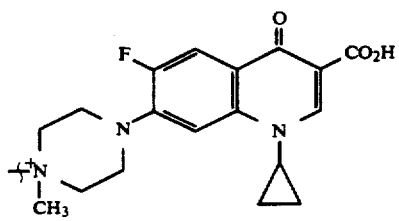

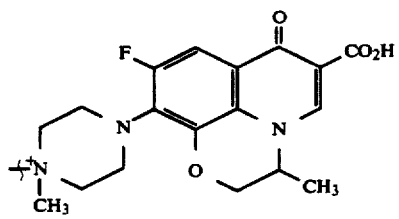

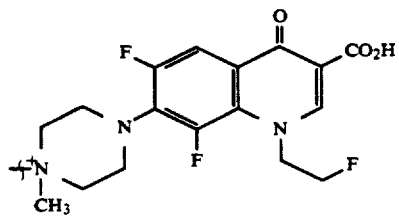

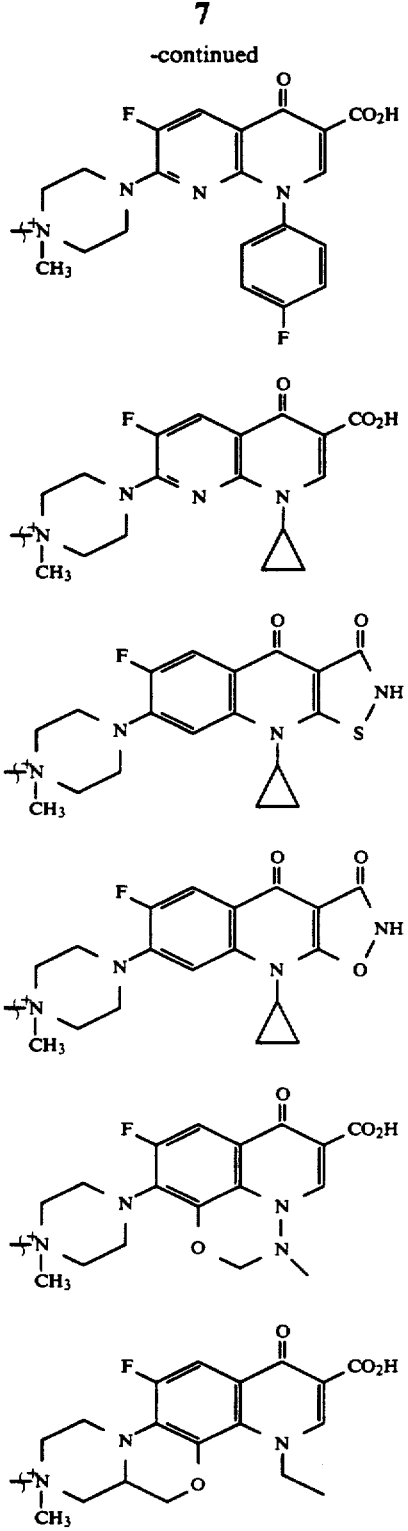

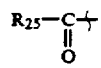

wherein $R_{25}$ is H or $C_1$ to $C_6$ lower alkanoic acid, e.g., acetyl, formyl, propionyl, butyryl and the like.

By the term "substituted phenyl" is meant phenyl mono- or di-substituted by halo(chloro, bromo, fluoro, etc.), lower alkyl, amino, nitro or trifluoromethyl.

By the term "substituted alkyl" is meant a "lower alkyl" moiety substituted by, for example, halo (chloro, fluoro. bromo, etc.), trifluoromethyl, amino, cyano, etc.

By the term "lower alkenyl" is meant straight or branched chain hydrocarbon groups which contain an olefinic double bond having 2 to 6 carbon atoms, i.e., the radical of compounds of the formula $C_nH_{2n}$ wherein n is 2 to 6, e.g. , allyl, vinyl, etc.

By the term "aralkyl" is meant a hydrocarbon group having both aromatic and aliphatic structures, that is, a hydrocarbon group in which a lower alkyl hydrogen atom is substituted by a monocyclic aryl group, e.g., phenyl, tolyl, etc.

The express ion 5- or 6- membered heterocyclic ring containing 1–4 hereto atoms selected from the group consisting of O, N and S is intended to represent the following groups: pyridyl, piperidyl, piperidino, N-oxido-pyridyl, pyrimidyl, piperazinyl, pyrolidinyl, pyridazinyl, N-oxide-pyridazinyl, etc. a 5-membered nitrogen-containing hereto ring, e.g. pyrazolyl, imidazolyl thiazolyl, 1,2,3-thiadiazolyl, 1,2,4-thiadiazolyl, 1,3,4-thiadiazolyl, 1,2,5-thiadiazolyl, 1,2,3-oxadiazolyl, 1,2,4-thiadiazolyl, 1,3,4-oxadiazolyl, 1,2,5-oxadiazolyl, 1,2,3-triazolyl, 1,2,4-triazolyl, 1H-tetrazolyl, 2H-tetrazolyl, etc., and others. Each of these hereto rings may be further substituted and, as the substituents, there may be mentioned, for example, lower alkyls such as methyl, ethyl propyl, etc., lower alkoxys such as methoxy, ethoxy, etc., halogens such as chlorine, bromine, etc., halogen substituted alkyls such as trifluoromethyl, trichloroethyl, etc., amino, mercapto, hydroxyl, carbamoyl, or carboxyl group, etc.

By the term "cycloloweralkyl" is meant a 3–6 membered saturated carboxylic moiety, e.g., cyclopropyl, cyclobutyl, cyclohexyl, etc.

As readily hydrolyzable esters of the compounds of formula I there are to be understood compounds of formula the carboxy group(s) of which (i.e., the 2-carboxy group) is/are present in the form of readily hydrolyzable ester groups. Examples of such esters, which can be of the conventional type, are the lower alkanoyloxyalkyl esters (e.g., the acetoxymethyl, pivaloyloxymethyl, 1-acetoxymethyl and 1-pivaloyloxyethyl ester), the lower alkoxycarbonyloxyalkyl esters (e.g., the methoxycarbonyloxymethyl, 1-ethoxycarbonyloxyethyl and 1-isopropoxycarbonyloxyethyl ester), the lactonyl esters (e.g., the phthalidyl and thiophthalidyl ester), the lower alkoxymethyl esters (e.g., the methoxymethyl ester) and the lower alkanoylaminomethyl esters (e.g., the acetamidomethyl ester). Other esters (e.g., the benzyl and cyanomethyl esters) can also be used.

By the term "aryl" is meant a substituted or unsubstituted aromatic moiety, such as phenyl, tolyl, xylyl, mesityl, cumenyl, naphthyl, and the like, wherein said aryl group may have 1 to 3 suitable substituents, such as halo (fluoro, chloro, bromo, etc.), hydroxy, and the like.

By the term "lower alkanoyl" or "alkanoyl" as utilized herein is intended a moiety of the formula Examples of salts of the compounds of formula I are alkali metal salts such as the sodium and potassium salt, the ammonium salt, alkaline earth metal salts such as the calcium salt, salts with organic bases such as salts with amines (e.g., salts with N-ethyl-piperidine, procaine, dibenzylamine, N,N'-dibenzylethylenediamine, alkylamines or dialkylamines) as well as salts with amino acids such as, for example, salts with arginine or lysine.

The terms "salts" and "pharmaceutically acceptable salts" as employed throughout this disclosure to refer to compounds of formula I also encompass zwitterions and other types of internal salts in which a carboxy group is negatively charged (i.e., lacks a hydrogen atom) and is neutralized by an accompanying positive charge within the molecule such as the positive charge on the quarternary nitrogen atom.

The compounds of formula I as well as their salts and readily hydrolyzable esters can be hydrates. The hydration can be effected in the course of the manufacturing process or can occur gradually as a result of hygroscopic properties of an initially anhydrous product.

A preferred class of compounds are of the formula

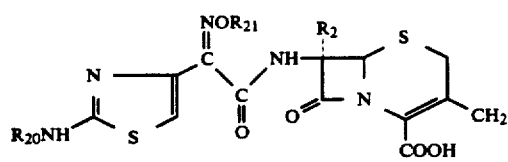

wherein $R_1$ and $R_2$ are as above, $R_{20}$ is hydrogen or an amino-protecting group, for example, trityl or chloroacetyl, and $R_{21}$ is hydrogen, lower alkyl or a group of the formula

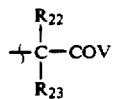

wherein $R_{22}$ and $R_{23}$ are as defined above and V is hydroxy or $NHR_{19}$ where $R_{19}$ is hydrogen or lower alkyl, amino, alkyl amino, aryl amino or acyl amino.

Still more preferred are compounds of the formula II, in which $R_{20}$ is hydrogen, and $R_{21}$ is methyl or a group of the formula

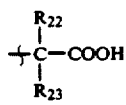

wherein $R_{22}$ and $R_{23}$ are selected from the group consisting of hydrogen and methyl.

Preferably, the

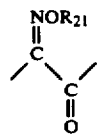

grouping is in the syn-form, e.g., the Z-form.

Another preferred class of compounds are those of the formula

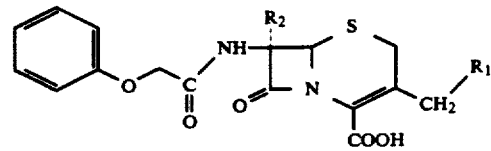

wherein $R_1$ and $R_2$ are as above.

Q is a substituted quinolinyl or naphthyridinyl group, preferably of the formula

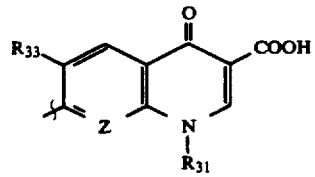

wherein Z represents C—$R_{30}$ or N, $R_{30}$ represents hydrogen, halogen or $R_{30}$ is an oxymethylene (—OCH$_2$—) bridge and wherein Q with its oxymethylene bridge and the piperazine nucleus form a fused six-membered ring.

$R_{31}$ represents hydrogen, lower alkyl, lower alkenyl, $C_3$-$C_7$ cycloalkyl, halo lower alkyl or mono-, di- and tri-halophenyl;

$R_{30}$ and $R_{31}$ when taken together represents lower alkylene of 3–5 carbon atoms, a lower alkylene monooxy group of 2–4 carbon atoms, a lower alkylene dioxy group having 1–2 carbon atoms or a group of the formula —OCH$_2$N(CH$_3$)—; and $R_{33}$ represents hydrogen or halogen.

In a preferred embodiment, Z is

wherein $R_{30}$ is hydrogen, chlorine or fluorine, most preferably hydrogen or flourine; and $R_{31}$ is lower alkyl, most preferably, ethyl or halogen substituted lower alkyl, most preferably, fluoroethyl, or alternatively, $C_3$-$C_7$-cycloalkyl, most preferably, cyclopropyl; and $R_{33}$ is chlorine or fluorine, preferably fluorine.

The compounds of Formula I, their pharmaceutically acceptable salts, and esters and hydrates of those compounds can be used as agents to combat bacterial infections (including urinary tract infections and respiratory infections) in mammalian species, for example, dogs, cats, horses, etc., and humans. These compounds exhibit activity against a broad range of both Gram-negative and Gram-positive bacteria.

The in vitro activity of the compounds of the present invention as measured by the Minimum Inhibitory Concentration (MIC) in micrograms/ml utilizing the Broth Dilution Method against a variety of Gram-positive and Gram-negative organisms, is as follows:

Concentration (MIC) in micrograms/ml utilizing the Broth Dilution Method against a variety of Gram-positive and Gram-negative organisms, is as follows:

Compound A: [6R-[6α,7β(Z)]]-1-[7-[[[(2-amino-4-thiazolyl)(methoxyimino)acetyl]amino]-2-carboxy-8-oxo-5-thia-1-azabicyclo[4.2.0]oct-2-en-3-yl]methyl]-4-[3-carboxy-6,8-difluoro-1-(2-fluoroethyl)-1,4-dihydro-4-oxo-7-quinolinyl]-1-methyl-piperazinium iodide Compound B: (6R-trans)-4-[3-carboxy-1-(2-fluoroethyl)-6,8-difluoro-1,4-dihydro-4-oxoquinolin-7-yl]-1-[[2-carboxy-8-oxo-7-[(phenoxyacetyl)amino]-5-thia-1-azabicyclo-[4.2.0]oct-2-en-3-yl]methyl]-1-methyl-piperazinium iodide Compound C: [6R-[6α,7β(Z)]]-1-[[7-[[[(2-amino-4-thiazolyl)[1-(1-carboxy-1-methyl)ethoxy]imino]acetyl]amino]-8-oxo-5-thia-1-azabicyclo-[4.2.0]oct-2-en-3-yl]methyl]-4-[3-carboxy-1-(2-fluoroethyl)-6,8-difluoro-1,4-dihydro-4-oxoquinolin-7-yl]-1-methyl-piperazinium hydroxide inner salt monosodium salt Compound D: [6R-[6α,7β(Z)]]-1-[[7-[[[(2-amino-4-thiazolyl)(methoxyimino)acetyl]amino]-2-carboxy-8-oxo-5-thia-1-azabicyclo[4.2.0]-oct-2-en-3-yl]methyl]-4-(3-carboxy-1-ethyl-6-fluoro-1,4-dihydro-4-oxo-7-quinolinyl)-1-methylpiperazinium iodide Compound E: (6R-trans)-4-[3-carboxy-6,8-difluoro-1-(2-fluoroethyl)-1,4-dihydro-7-quinolinyl]-1-[[2-carboxy-7-(formylamino)-8-oxo-5-thia-1-azabicyclo[4.2.0]oct-2-en-3-yl]methyl]-1-methylpiperazinium trifluoroacetate salt

TABLE 1

| | In Vitro MIC (µg/ml), Broth Dilution Method | | | | |
|---|---|---|---|---|---|
| | Compounds | | | | |
| Culture | A | B | C | D | E |
| E. coli ATCC 25922 | 0.25 | 0.5 | 0.25 | 0.5 | 0.5 |
| E. coli TEM 1 | 0.25 | 0.5 | 0.5 | 0.5 | 0.5 |
| E. cloacae 5699 | 0.5 | 0.5 | 0.5 | 1 | 0.5 |
| E. cloacae P99 | 0.5 | 0.5 | 2 | 1 | 0.5 |
| S. marcescens 1071 | 0.5 | 0.5 | 0.5 | 0.5 | 1 |
| P. aeruginosa 8710 | 8 | 8 | 8 | 8 | 8 |
| P. aeruginosa 18 S/H | 8 | 4 | 8 | 32 | 8 |
| E. faecalis ATCC 29212 | 64 | 32 | 32 | 32 | 32 |
| S. pneumoniae 6301 | 0.063 | 0.25 | 1 | 0.063 | 1 |
| S. aureus 1059B | 2 | 0.5 | 8 | 2 | 0.5 |
| S. aureus 95 | 4 | 1 | 4 | 4 | 1 |
| S. aureus ATCC 29213 | 4 | 0.5 | 4 | 4 | 0.5 |

For combatting bacterial infections in mammals, a compound of this invention (more precisely, a compound of formula I where R is hydrogen or a corresponding hydrolyzable ester or pharmaceutically acceptable salt or hydrate) can be administered to a mammal in an amount of about 5 mg/kg/day to about 500 mg/kg/day, preferably about 10 mg/kg/day to 100 mg/kg/day, most preferably about 10 mg/kg/day to about 55 mg/kg/day.

Modes of administration which have been used in the past to deliver penicillins and cephalosporins to the site of the infection are also contemplated for use with the compounds of the present invention. By way of illustration, such methods of administration include parenteral, e.g., intravenous or intramuscular, and enteral, e.g., as a suppository.

The following reaction schemes set forth the methods and intermediates useful in producing the end products of formula I. Unless otherwise noted, $R_2$, $R_3$ and Q are as previously defined.

The compound of formula IV, referred to in the Schemes, is a substituted piperazine of the formula

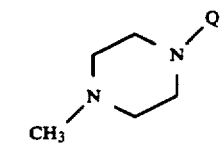

in which the pipefarine nucleus may be substituted with one or more lower alkyl groups of 1-8, preferably 1-4 carbon atoms. It shall be understood that in these reaction schemes substituted piperazines of the structure

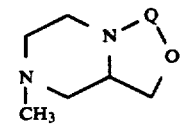

may similarly be used as starting materials in place of IV.

In the following reaction sequences, where a substituent group is present which may be attacked during the reaction it should be in protected form, utilizing well known protecting groups. For example, amino groups may be protected with easily removable protective groups employed in peptide chemistry, such as a triphenylmethyl group.

As ester protecting groups one may utilize an ester form which can be easily converted into a free carboxyl group under mild conditions. The ester protecting group can be, for example, t-butyl, p-nitrobenzyl, allyl, etc. Also suitable are trimethylsilyl esters.

Scheme I

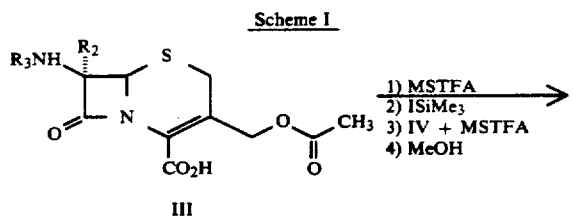

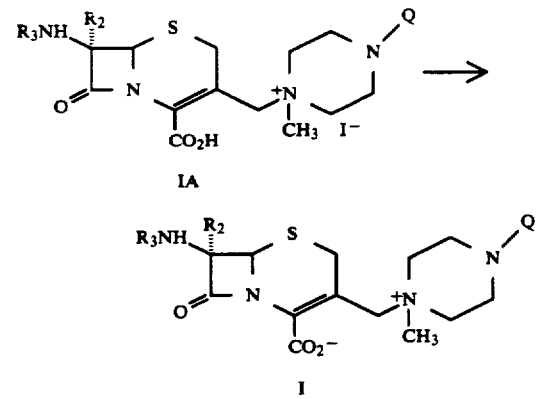

SCHEME I

The compound of formula III is initially protected by reaction with a trimethylsilating agent such as N-methyl-N-(trimethylsilyl)trifluoroacetamide (MSTFA) in an inert solvent such as chloroform or methylene chloride. The resulting trimethylsilyl ester, in which all potentially reactive sites, such as amino, hydroxy, and carboxylic acid functions, are protected by trimethylsilyl groups, is then subjected to a reaction with iodotrimethylsilane at about 0° C. to room temperature, over a period of about twenty minutes to about two hours. The reaction mixture is then concentrated to dryness under reduced pressure, and the residue is dissolved in a suitable non-hydroxylic solvent such as acetonitrile. A small amount of tetrahydrofuran (THF) is introduced to decompose any residual traces of iodotrimethylsilane. The resulting protected iodo intermediate is then further reacted in situ with a protected form of the pipefarine derivative IV which is obtained from IV by treatment with a trimethylsilating agent such as MBTFA in a compatible solvent such as acetonitrile. The quaternization reaction is conducted at about room temperature over a period of about 30 minutes to 24 hours, preferably about 2 hours. Addition of a hydroxylic solvent such as methanol, with ice-cooling, then causes solvolysis of the trimethylsilyl protecting groups, and the quaternary iodide of formula IA precipitates. Further treatment under aqueous conditions with a base such as sodium bicarbonate or sodium hydroxide, or with sodium phosphate buffer, converts IA to the zwitterionic form I in which, depending upon the amount of base added, or the pH of the buffer, other acidic functions in the $R_3$ and Q substituents can be converted to salts.

trile. The quaternization reaction is allowed to proceed for about 30 minutes to 24 hours, preferably about two to four hours, and most preferably at room temperature. Then, an acylating agent consisting of an activated form of a carboxylic acid, for example, a thio ester such as

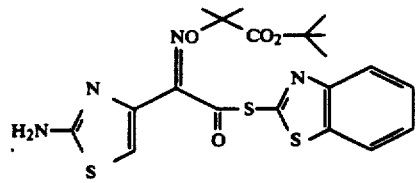

is added, The reaction mixture is then stirred for a period of from 2 to 24 hours. The mixture is then concentrated to dryness under reduced pressure, and the residue is redissolved in acetonitrile. Addition of methanol then solvolyzes the trimethylsilyl protecting groups and precipitates the quaternary iodide of formula IA. In the case where other protecting groups are present for example, in the substituent $R_3$, those protecting groups are then removed by methods known in the art. For example, if a tert.-butyl eater is present, it is cleaved by treatment with trifluoroacetic acid-anisole. Finally, as in Scheme I, the product of formula I is obtained after aqueous reaction with a base such as sodium bicarbonate or sodium phosphate buffer.

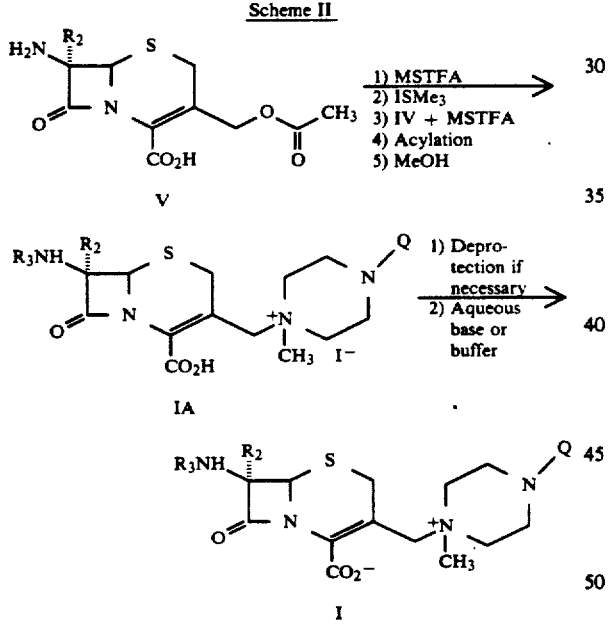

SCHEME II

Starting material of structure V is subjected initially to reaction with a trimethylsilating agent such as MSTFA in an inert solvent such as acetonitrile under anhydrous conditions at room temperature for a period of about 10 minutes to two hours, preferably about 30 minutes. Iodotrimetylsilane is then added and allowed to react for from 15 minutes to three hours, preferably about 30 minutes, at room temperature. A small amount of THF is then added, to decompose any residual iodotrimethylsilane. The guaternization step is then carried out by adding a protected form of the pipefarine derivative of IV which is obtained from a compound of formula IV by treatment with a trimethylsilating agent such as MSTFA in a suitable solvent such as acetoni-

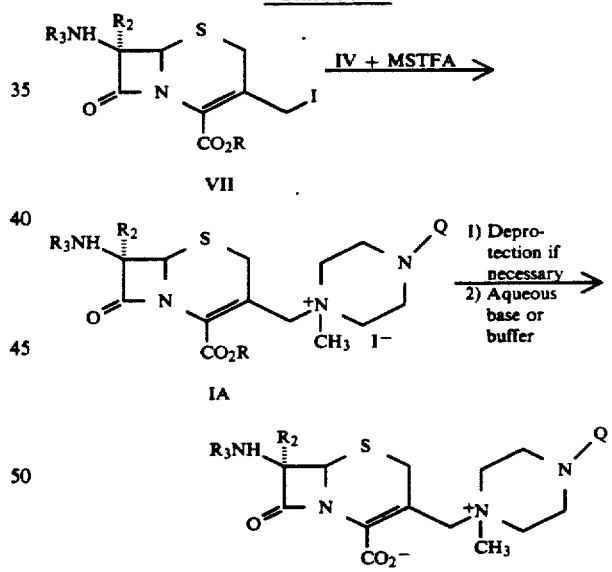

SCHEME III

Compounds of formula VII which are starting materials for this scheme are prepared by the procedures described in U.S. Pat. No. 4,266,049 (R. Bonjouklian, May 5, 1981). In this sequence, the pipefarine derivative of formula IV is converted to a protected form by reaction with a trimethylsilating agent such as MSTFA in a suitable solvent, such as acetonitrile, under anhydrous conditions. Alternatively, conventional protecting groups which are readily removable under mild conditions can be used to protect reactive functionalities in the piperazine derivative of formula IV. For example, a carboxylic acid can be protected as a tert, butyl or p-nitrobenzyl ester. The reaction of VII with the protected form of IV in an inert solvent such as acetonitrile provides the quaternary iodide IA. Further treatment as necessary removes the protecting groups; for example, when R is tert. butyl, the ester is cleaved with trifluoroacetic acid-anisole. Subsequent treatment with aqueous sodium bicarbonate or sodium phosphate buffer gives a compound of formula I, which other carboxylic acid functions in $R_3$ or Q may be converted to salts, depending upon the pH.

Compounds of formula I in which m is 1(sulfoxides) or 2(sulfones) are prepared from compounds of formula I in which m is 0, using oxidation procedures known to those skilled in the art, for example, oxidation with meta-chloroperoxybenzoic acid.

The invention is further illustrated in the following examples, which are not intended to be limiting.

EXAMPLE 1

Preparation of

[6R-trans]-4-[3-carboxy-1-(2-fluoroethyl)-6,8-difluoro-1,4-dihydro-4-oxoquinolin-7-yl]-1-[[2-carboxy-8-oxo-7-[(phenoxyacetyl)amino]-5-thia-1-azabicyclo[4.2.0]oct-2-en-3-yl]methyl]-1-methylpiperazinium iodide

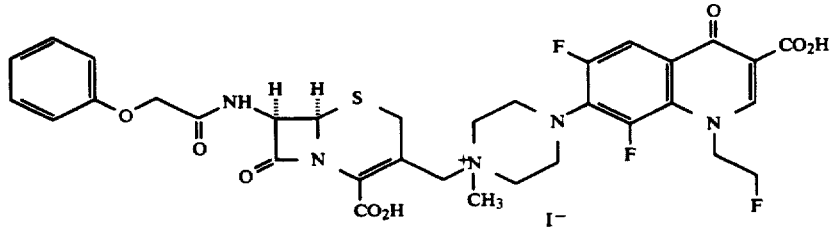

Under an argon atmosphere, a mixture of 406 mg (1 mmol) of [6R-trans]-3-(acetyloxy)methyl]-8-oxo-7-[(phenoxyacetyl)amino]-5-thia-1-azabicyclo[4.2.0]-oct-2-en-2-carboxylic acid, 2 mL of dry methylene chloride, a nd 0.60 mL (3 mmol) of N-methyl-N-(trimethylsilyl)-trifluoroacetamide (MSTFA) was stirred for one hour: 0.28 mL (2 mmol) of iodotrimethylsilane was then added, and the mixture stirred for 2 hours. The solution was then concentrated to dryness under reduced pressure, and the residual oil dissolved in 2 mL of acetonitrile. Five drops of anhydrous THF were added, and the mixture was stirred for 5-10 minutes. A solution prepared from 111 mg (0.3 mmol) of 6,8-difluoro-1-(2-fluoroethyl)-1,4-dihydro-7-(4-methyl-1-piperazinyl)-4-oxo-3-quinolinecarboxylic acid, 0.11 mL (0.6 mmol) of MSTFA and 1 mL of acetonitrile was added, and stirring was continued for 2 hours. The mixture was chilled in ice, and approximately 100 mg of methanol were added. The solid which precipitated was filtered, washed with acetonitrile, and dried under reduced pressure to obtain the title compound: NMR ($Me_2SO-d_6$) δ 3.15 (s, 3H, $NCH_3$), 3.45–3.85 (m, 9H, 4 x $NCH_2$ and CH of $SCH_2$), 3.95 (d, 1H, J gem = 16.5 Hz, CH of $SCH_2$), 4.39 and 4.77 (AB, 2H, J gem = 13 Hz, $NCH_2$). 4.61 and 4.64 (AB, 2H, J gem = 15 Hz, $OCH_2CO$), 4.83–5.07 (m, 4H, $NCH_2CH_2F$), 5.24 (d, 1H, J = 5Hz, CH), 5.82 (dd, 1H, J = 5 and 7 Hz, CH), 6.95 (d, 2H, J = 8 Hz, Ar), 6.97 (t, 1H, J = 8 Hz, Ar), 7.29 (t, 2H, J = 8 Hz), 7.96 (d, 1 H, J = 12 Hz, Ar), 8.91 (s, 1H, =CH—), 9.18 (d, 1H, J = 7 Hz, NH); IR (KBr) 3400, 1788, 1728, 1700, 1612, $cm^{-1}$; mass spectrum m/z 716 (cation).

EXAMPLE 2

Preparation of [6R-[6α,7β(Z)]]-1-[[7-[[[(2-amino-4-thiazolyl)[1-(1-carboxy-1-methyl)ethoxy]imino]acetyl]amino]-8-oxo-5-thia-1-azabicyclo[4.2.0]oct-2-en-3-F1]methyl]-4-[3-carboxy-1-(2-fluoroethyl)-6,8-difluoro-1,4,dihydro-4-oxoquinolin-7-yl]-1-methylpiperazinium hydroxide inner salt monosodium salt

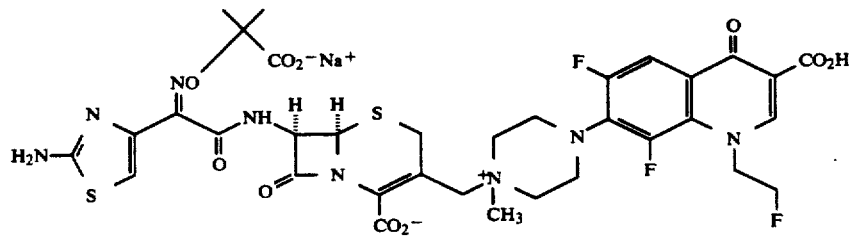

Under an argon atmosphere, a mixture of 5.12 g (8 mmol) of [6R-[6α,7β(Z)]]-3-[(acetyloxy)methyl]-7-[[[(2-amino-4-thiazolyl)[1-(1-carboxy-1-methyl)ethoxy]imino]acetyl]amino]-8-oxo-5-thia-1-azabicyclo[4.2.0]oct-2-ene-2-carboxylic acid trifluoroacetic acid salt, 48 mL of dry acetonitrile, and 12 mL (64 mmol) of MSTFA was stirred for 30 minutes: 2.0 mL (14 mmol) of iodotrimethylsilane was added dropwise, and the mixture was stirred for 30 minutes. With momentary cooling in ice, 1.12 mL (14 mmol) of dry THF was added. After 10 minutes, a solution prepared from 2.27 g (6 mmol) of 6,8-difluoro-1-(2-fluoroethyl)-1,4-dihydro-7-(4-methyl-1-piperazinyl)-4-oxo-3-quinolinecarboxylic acid, 24 mL of acetonitrile, and 1.28 mL (7.2 mmol) of MSTFA was added, and the mixture stirred for 1.5 hours. The mixture was concentrated under reduced pressure, and the residual oil was dissolved in 40 mL of acetonitrile. With ice-cooling, 4 mL of methanol were added, resulting in a thick precipitate. After settling for a few minutes, the precipitate was filtered, and washed with four 10 mL portions of acetonitrile. After drying, the solid was triturated with 60 mL of methanol, filtered, and washed with four 10 mL portions of methanol. The solid (5.7 g) thus obtained, was suspended in water, and aqueous sodium bicarbonate was added to bring the pH to 7. The solution of crude product was purified by $C_{18}$ reverse phase HPLC in three steps. First a column of 50 g of Waters $C_{18}$-silica was used, with water followed by 30% acetonitrile in water as eluant. Then, using a 0.025 molar pH 7 buffer-acetonitrile gradient, the product was further purified by HPLC on a Waters Prep 500A with $C_{18}$ columns. Finally, the product was desalted on a flash column of 60 g of $C_{18}$ silica with water and 20% acetonitrile in water as eluants. After concentrating under reduced pressure to eliminate the organic solvent, and freeze-drying, 1.0 g of the title compound was obtained: NMR ($Me_2SO$-$d_6$-$D_2O$) 1.37 (s, 3H, $CH_3$), 1.44 (s, 3H, $CH_3$), 3.10 (s, 3H, $NCH_3$), 3.39 and 3.88 (AB, 2H, J gem=16.5 Hz, $SCH_2$), 3.40–3.70 (m, 8H, 4 x $NCH_2$), 4.12 and 5.17 (AB, 2H, J gem=12.5 Hr, $NCH_2$) 4.62–4.94 (m, 4H, $NCH_2CH_2F$), 5.15 (d, J=5Hz, CH), 5.73 (d, 1H, J=5 Hz, CH) 6.74 (s, 1H, Ar), 7.83 (d, 1H, J=12 Hz, Ar), 8.47 (brs, 1H, =CH—); IR (KBr) 3400, 1772, 1618, 1595 cm$^{-1}$; mass spectrum m/z=859 (M+H)$^+$.

EXAMPLE 3

Preparation of [6R-[6α,7β(Z)]]-1-[[7-[[(2-amino-4-thiazolyl)(methoxyimino)acetyl]amino]-2-carboxy-8-oxo-8-thia-1-azabicyclo[4.2.0]-oct-2-en-3-yl]methyl]-4-(3-carboxy-1-ethyl-6-fluoro-1,4-dihydro-4-oxo-7-quinolinyl)-1-methylpiperazinium iodide

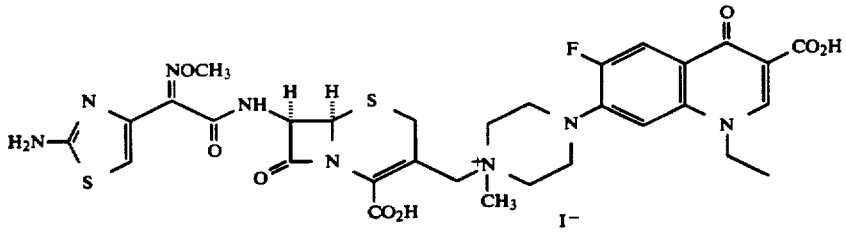

Under an argon atmosphere, a mixture of 273 mg (0.6 mmol) of [6R-[6α,7β(Z)]]-3-[(acetyloxy)methyl]-7-[[(2-amino-4-thiazolyl)(methoxyimino)acetyl]amino]-8-oxo-5-thia-1-azabicyclo[4.2.0]oct-2-ene-2-carboxylic acid, 2 mL of dry methylene chloride, and 0.45 mL (2.4 retool) of MSTFA was stirred for 2 hours; 0.17 mL (1.2 mmol) of iodotrimethylsilane was added, and stirring was continued for another 2 hours. The mixture was concentrated under reduced pressure, and the residual oil was dissolved in 2 mL of dry acetonitrile. A few drops of dry THF were added, and the mixture stirred for 15 minutes. A solution prepared from 60 mg (0.18 mmol) of 1-ethyl-6-fluoro-1,4-dihydro-7-(4-methyl-1-piperazinyl)-4-oxo-3-quinolinecarboxylic acid, 1 mL of dry acetonitrile, and 0.07 mL (0.36 mmol) of MSTFA was added, and stirring was continued for 2 hours. Dropwise addition of 125 mg of methanol caused the product to precipitate. The solid was filtered, washed with four 1-mL portions of acetonitrile, and dried under reduced pressure. After trituration with methanol and drying under reduced pressure, the title compound was obtained: NMR ($Me_2SO$-$d_6$) δ 1.45 (brt, 3H, $CH_3$ of NEt), 3.15 (s, 3H, $NCH_3$), 3.50–3.95 (m, 9H, 4 x $NCH_2$ and CH of $SCH_2$), 3.85 (s, 3H, $OCH_3$), 3.99 (d, 1H, J gem=16.5 Hz, CH of $SCH_2$), 4.43 and 4.70 (AB, 2H, J gem=14 Hz, $NCH_2$), 4.61 (brq, 2H, $CH_2$ of NEt), 5.31 (d, 1H, J=5 Hz, CH), 5.94 (dd, 1H, J=5 and 8 Hz, CH), 6.76 (s, 1H, Ar), 7.30 (br, 2H, $NH_2$), 7.31 (d, 1H, J=6.5 Hz, Ar), 8.03 (d, 1H, J=12.5 Hz, Ar), 9.03 (s, 1H, =CH—), 9.68 (d, 1H, J=8 Hz, NH); IR (KBr) 1785, 1720, 1680, 1628, cm$^{-1}$; mass spectrum m/z=729 (cation).

EXAMPLE 4

Preparation of [6R-[6α,7β(Z)]]1,1-[7-f[[(2-amino-4-thiazolyl)(methoxyimino)acetyl]amino]-2-carboxy-8-oxo-5-thia-1-azabicyclo[4.2.0]oct-2-en-3-yl]methyl]-4-[3-carboxy-6,8-difluoro-1-(2-fluoroethyl)-1,4-dihydro-4-oxo-7-quinolinyl]-1-methylpiperazinium iodide

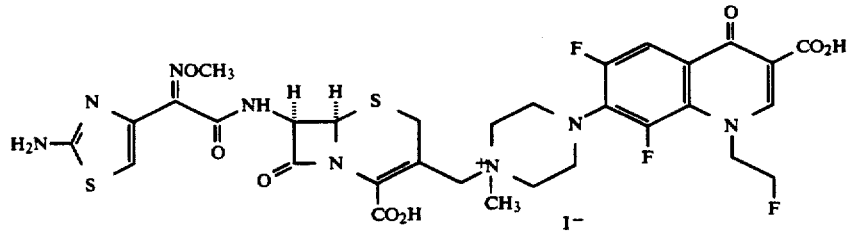

A mixture of 84.6 mg (0.186 mmol) of [SR-[6α,7β(Z)]]-3-[(acetyloxy)methyl]-7-[[(2-amino-4-thiazolyl)(methoxyimino)acetyl]amino]-8-oxo-5-thia-1-azabicyclo[4.2.0]oct-2-ene-2-carboxylic acid, 4 mL of dry methylene chloride, and 0.148 mL (0.8 mmol) of MSTFA was stirred for one hour. To the resulting solution was added 0.0625 mL (0.46 mmol) of iodotrimethylsilane. The mixture was stirred for 2 hours, and concentrated to dryness under reduced pressure. The residue was dissolved in 2 mL of dry acetonitrile, and a few drops of dry THF were added. The mixture was stirred for 3 minutes, and then a solution prepared from 36.9 mg (0.10 mmol) of 6,8-difluro-1-(2-fluoroethyl)-1,4-dihydro-7-(4-methyl-1-Piperazinyl)-4-oxo-3-guinoline carboxylic acid, 0.040 mL (0.215 mmol) of MSTFA, and 2.0 mL of dry acetonitrile was added. The mixture was stirred for 3 hours. After addition of 0.50 mL of methanol a precipitate formed. The solid was filtered, washed repeatedly with acetonitrile, and dried to obtain 87.5 mg of the title compound: NMR (Me$_2$SO-d$_6$) δ 3.15 (s, 3H, NCH$_3$), 3.50–3.90 (m, 9H, 4 x NCH$_2$ and CH of SCH$_2$), 3.86 (s, 3H, OCH$_3$), 3.96 (d, 1H, J gem=17 Hz CH of SCH$_2$) 4.42 and 4.73 (AB, 2H, J gem=14 Hz, NCH$_2$), 4.85–5.10 (m, 4H, NCH$_2$CH$_2$F), 5.29 (d, 1H, J=5 Hz, CH), 5.93 (dd, 1H, J=5 and 7 Hz, CH), 6.86 (s, 1H, Ar), 7.24 (s, 2H, NH$_2$), 7.98 (d, 1H, J=12 Hz, Ar), 8.94 (s, 1H =CH—), 9.67 (d, 1H, J=7 Hz, NH); IR (KBr) 3420, 1775, 1720, 1775, 1618 cm$^{-1}$.

(d, 1H, J=7 Hz, NH); IR (KBr) 3410, 1772, 1665, 1618 cm$^{-1}$; mass spectrum m/z 787 (M+H)$^+$.

EXAMPLE 6

Preparation of (6R-trans)-4-[3-carboxy-6,8-difluoro-1-(2-fluoroethyl)-1,4-dihydro-7-quinolinyl]-1-[[2-(1,1-dimethylethoxy)-carbonyl-7-(formylamino)-8-oxo-5-thia-1-azabicyclo[4.2.0.]-oct-2-en-3-yl]-methyl]-1-methylpiperazinium iodide

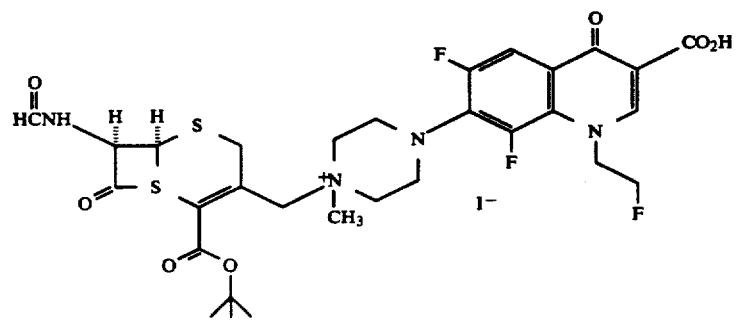

EXAMPLE 5

Preparation of 6R-[6α,7β(Z)-1-[7-[[[(2-amino-4-thiazolyl)(methoxyimino)acetyl]amino]-2-carboxy-8-oxo-5-thia-1-azabicyclo[4.2.0]oct-2-en-3-yl]methyl]-4-[3-carboxy-6,8-difluoro-1-(2-fluoroethyl)-1,4-dihydro-4-oxo-7-quinolinyl]-1-methylpiperazinium monosodium salt A mixture of 0.87 g (2.35 mmol) of 6,8-difluoro-1-(2-fluoroethyl)-1,4-dihydro-7-(4-methyl-1-piperazinyl)-4-oxo-3-quinolinecarboxylic acid, 0.51 mL (2.6 mmol) of MSTFA, and 5 mL of dry acetonitrile was stirred for 30 minutes; 1.00 g of [6R (6α,7β]-7-formylamino-3-iodomethyl-8-oxo-5-thia-1-azabicyclo[4.2.0]oct-2-ene-2 carboxylic acid 1,1-dimethylethyl ester was added, and

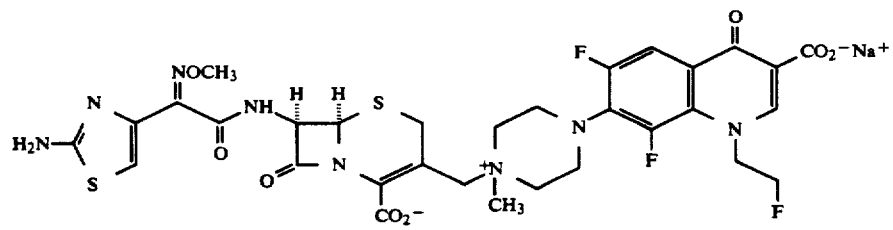

A suspension of 900 mg of the compound prepared in Example 4 in water was neutralized with 0.1N sodium hydroxide, and the resulting solution was freeze-dried. The residue was purified by C$_{18}$ reverse phase HPLC on a Waters Prep 500A, eluting with a water-acetonitrile gradient (0–40%). Evaporation and lyophilization of the appropriate fractions afforded 344 mg of the title compound: NMR (Me$_2$SO-d$_6$) δ 3.10 (e, 3H, NCH$_3$), 3.40–3.76 (m 9H 4 x NCH$_2$ and CH of SCH$_2$), 3.84 (d, 1H, J=16 Hz, CH of SCH$_2$), 3.84 (e, 3H, OCH$_3$), 4.10 and 5.19 (AB, 2H, J gem=14 Hz), 4.70–4.94 (m, 4H, NCH$_2$CH$_2$F), 5.13 (d, 1H, J=5 Hz, CH), 5.65 (dd, 1H, J=5 and 7 Hz, CH), 6.74 (s, 1H, Ar), 7.23 (S, 2H, NH$_2$), 7.82 (d, 1H, J=12 Hz, Ar), 8.55 (e, 1H, =CH—), 9.58 stirring was continued for 24 hours. The resulting precipitate was filtered, and discarded. The mother liquor was absorbed onto a column of 5 g of C$_{18}$-silica. After elution with water, 10%- and 20%- aqueous methanol o the appropriate fractions were combined and concentrated under reduced pressure to yield a precipitate. After filtration and drying, 380 mg of the title compound was obtained: IR (KBr) 3440, 1785, 1720, 1610 cm$^{-1}$; mass spectrum m/z=666 (cation).

EXAMPLE 7

Preparation of
(6R-trans)-4-[3-carboxy-6,8-difluoro-1-(2-fluoroethyl-)-1,4-dihydro-7-quinolinyl]-1-[[2-carboxy-7-(formylamino)-8-oxo-5-thia-1-azabicyclo[4.2.0]oct-2-en-3-yl]-methyl]-1-methylpiperazinium trifluoroacetate salt momentarily, and 0.14 mL (1.75 mmol) of anhydrous THF was added. After 10 minutes, a solution prepared from 277 mg (0.75 mmol) of 6,8-difluoro-1-(2-fluoroethyl)-1,4-dihydro-7-(4-methyl-1-piperazinyl)-4-oxo-3-quinolinecarboxylic acid, 0.17 mL (0.9 mmol) of MSTFA and 3 mL of dry acetonitrile was added. Stirring at room temperature was continued for 2.5 hours:

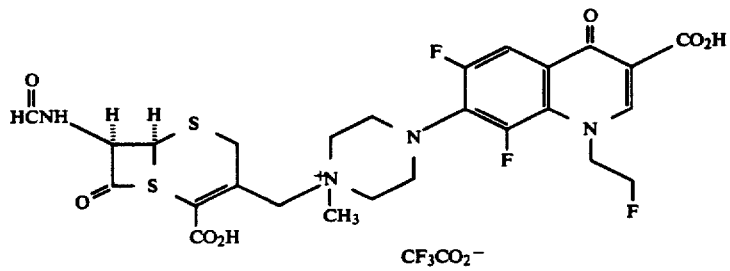

A mixture of 200 mg of the compound from Example 6, 0.2 mL anisole, and 2.5 mL of trifluoroacetic acid was stirred for 3 hours at room temperature. After filtration of the insoluble portion, the solution was concentrated under reduced pressure. The residue was dissolved in 10 mL of acetonitrile, and 200 mL of ether was added to precipitate the product. After filtration and drying, 135 mg of the title compound was obtained: NMR (Me$_2$SO-d$_6$) δ 3.14 (s, 3H, NCH$_3$), 3.50–3.85 (m, 9H, 4 x NCH$_2$ and CH of SCH$_2$), 3.95 (d, 1H, J gem=16.5 Hz, CH of SCH$_2$), 4.35 (d, 1H, J gem=13 Hz, CH of NCH$_2$), 4.82–5.05 (m, 5H, NCH$_2$CH$_2$F and CH of NCH$_2$), 5.23 (d, 1H, J=5Hz, CH), 5.84 (dd, 1H, J=5 and 7 Hz, CH), 7.96 (d, 1H, J=13 Hz, Ar), 8.17 (s, 1H, NCHO), 8.92 (s, 1H, =CH—), 9.11 (d, 1H, J=7 Hz, NH); IR 3400, 1780, 1720, 1685 cm$^{-1}$; mass spectrum m/z=610 (cation).

EXAMPLE 8

Preparation of
[6R-[6α,7β(Z)]]-1-[[7-[[(2-amino-4-thiazolyl)[[1,1-dimethyl-2-(1,1-dimethylethoxy)-2-oxoethoxy]imino]acetyl]amino]-8-oxo-5-thia-1-azabicyclo[4.2.0]oct-2-en-3-yl]methyl]-4-[3-carboxy-(2-fluoroethyl)-6,8-difluoro-1,4-dihydro-4-oxoquinolin-7-yl]-1-methylpiperazinium iodide 478 mg (1 mmol) of 2-[[[1-(2-amino-4-thiazolyl)-2-[(2-benzothiazolyl)thio]-2-oxoethylidene]amino]oxy]methylpropanoic acid 1,1-dimethylethyl ester and 4 mL of dry acetonitrile were added, and the mixture was stirred overnight. After filtration to remove a small amount of insoluble solid, the mixture was concentrated to dryness under reduced pressure. The residual oil was redissolved in 4 mL of acetonitrile, and with ice cooling, 0.16 mL of methanol was added. After stirring for one minute and standing for 3 minutes, the precipitated solid was filtered. After washing with three 3-mL portions of acetonitrile, and drying under pressure, 530 mg of the title compound was obtained: NMR (Me$_2$SO-d$_6$), δ 1.36 (s, 12H, t-Bu and CH$_3$), 1.40 (s, 3H, CH$_3$), 3.12 (s, 3H, NCH$_3$), 3.40–3.86 (m, 9H, 4 x NCH$_2$ and CH of SCH$_2$), 3.96 (d, 1H, J gem=16 Hz, CH of SCH$_2$), 4.40–4.66 (AB, 2H, J gem=13 Hz, NCH$_2$), 4.62–5.06 (m, 4H, NCH$_2$CH$_2$F), 5.26 (d, 1H, J=5 Hz, CH), 5.93 (dd, 1H, J=5 and 7 Hz, CH), 6.68 (s, 1H, Ar), 7.25 (s, 2H, NH$_2$), 7.92 (d, 1H, J=12 Hz, Ar), 8.88 (s, 1H, =CH—), 9.44 (d, 1H, J=7 Hz, NH).

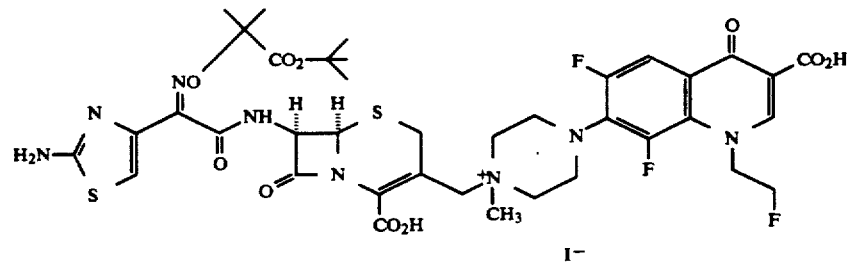

Under an argon atmosphere, a mixture of 272 mg (1 mmol) of 7-aminocephalosporanic acid, 0.67 mL (3.6 mmol) of MSTFA and 3 mL of dry acetonitrile was stirred for 30 minutes; 0.25 mL (1.75 mmol) of iodotrimethylsilane was then added and stirring was continued for another 30 minutes. The mixture was cooled

EXAMPLE 9

Alternate Synthesis of
[6R-[6α,7β(Z)]]-1-[7-[[[(2-amino-4-thiazolyl)[1-(1-carboxy-1-methyl)ethoxy]imino]acetyl]amino]-8-oxo-5-thia-1-azabicyclo[4.2.0]oct-2-en-3-yl]methyl]-4-[3-carbox]-1-(2-fluoroethyl)-6,8-difluoro-1,4-dihydro-4-oxoquinolin-7-yl]-1-methylpiperazinium hydroxide inner salt monosodium salt

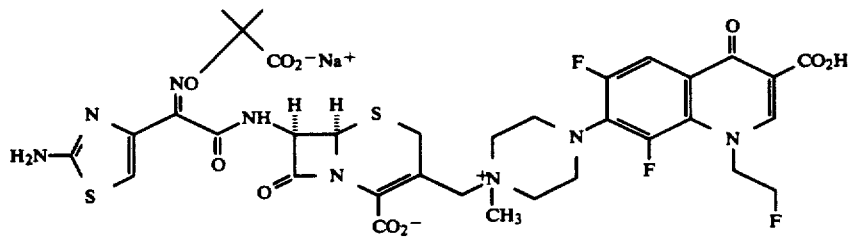

A solution of 1 02 mg of the compound prepared in-Example 8 in 0.4 mL of anisole, 1.5 mL of methylene chloride, and 1.5 mL of trifluoroacetic acid was kept overnight at 0° C. After filtering, concentrating to dryness under reduced pressure, adding methylene chloride and again concentrating to dryness, the residue was triturated with ether to obtain a solid. The solid was dissolved in sodium phosphate buffer of pH 7, and purified by reverse phase HPLC, to obtain the title compound having an NMR spectrum similar to that of the product obtained by the previously described route (Example 2).

What is claimed is:

1. A compound of formula

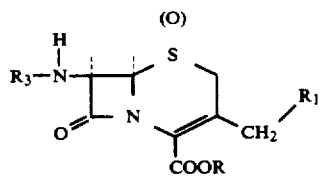

wherein R is hydrogen or a carboxylic acid-protecting group; $R_1$ is a piperazinium group of formula

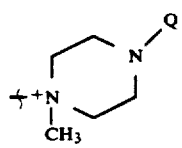

wherein Q represents a substituted quinolonyl or naphthyridonyl group and the piperazine nucleus may be unsubstituted or substituted with one or more lower alkyl groups; $R_2$ is selected from the group consisting of hydrogen, lower alkoxy, lower alkylthio and amido; $R_3$ is an acyl group; and m is 0, 1 or 2;

or a corresponding readily hydrolyzable ester, pharmaceutically acceptable salt or hydrate thereof.

2. A compound as in claim 1 wherein m is zero and $R_2$ is hydrogen.

3. A compound as in claim 2 wherein Q is:

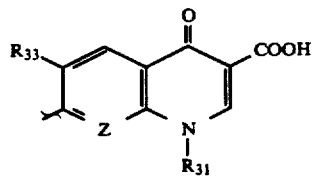

wherein Z represents

or N, $R_{30}$ represents hydrogen or halogen or $R_{30}$ is a oxymethylene (—OCH$_2$—) bridge and wherein Q with its oxymethylene bridge and the piperazine nucleus form a fused six-membered ring; $R_{31}$ represents hydrogen, lower alkyl, lower alkenyl, $C_3$-$C_7$ cycloalkyl, halo lower alkyl or mono-, di- and tri-halophenyl; $R_{30}$ and $R_{31}$ when taken together represents lower alkylene of 3-5 carbon atoms, a lower alkylene mono-oxy group of 2-4 carbon atoms, a lower alkylene dioxy group having 1-2 carbon atoms or a group of the formula —OCH$_2$, N(CH$_3$)—, and $R_{33}$ represents hydrogen or halogen.

4. A compound as in claim 3, wherein Z is

in which $R_{30}$ is hydrogen, bromine, chlorine or fluorine, $R_{31}$ is lower alkyl, halo-lower alkyl or $C_3$-$C_7$ cycloalkyl, and $R_{33}$ is hydrogen, chlorine or fluorine.

5. A compound as in claim 4, wherein $R_{30}$ is hydrogen or fluorine, $R_{31}$ is ethyl, fluoroethyl or cyclopropyl, and $R_{33}$ is hydrogen or fluorine.

6. A compound as in claim 1, wherein $R_1$ is of the formula

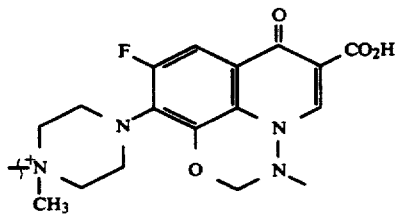

7. A compound as in claim 1, wherein $R_1$ is of the formula

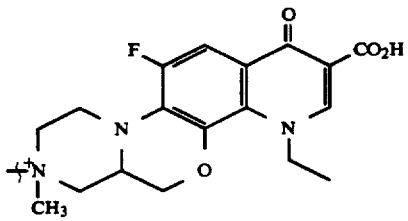

8. A compound as in claim 1 wherein acyl group $R_3$ is an aliphatic group of the formula

wherein $R_5$ is selected from the group consisting of hydrogen, alkyl, cycloalkyl, alkoxy, alkenyl, cycloalkenyl, cyclohexadienyl, or alkyl or alkenyl substituted with one or more halogen, cyano, nitro, amino, mercapto, alkylthio, or cyanomethylthio groups.

9. A compound as in claim 1 wherein $R_3$ is an aromatic acyl group selected from the group consisting of

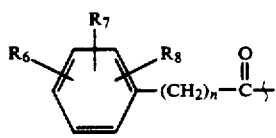

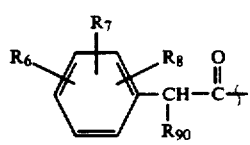

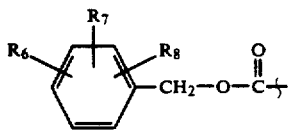

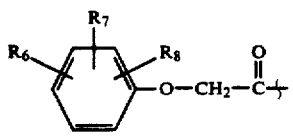

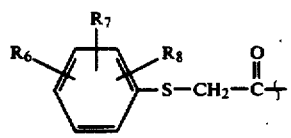

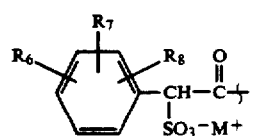

-continued

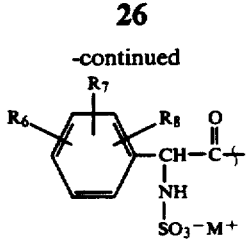

wherein n is 0, 1, 2 or 3; $R_6$, $R_7$, and $R_8$ are independently selected from the group consisting of hydrogen, halogen, hydroxyl, nitro, amino, cyano, trifluoromethyl, alkyl of 1 to 4 carbon atoms, alkoxy of 1 to 4 carbon atoms or aminomethyl; and $R_{90}$ is selected from the group consisting of amino, acylamino, hydroxyl, a carboxyl salt, protected carboxy, azido or a sulfo salt.

10. A compound as in claim 1 wherein acyl group $R_3$ is a heteroaromatic group selected from the group consisting of

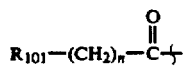

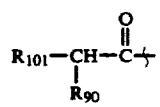

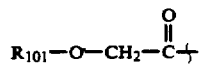

, and

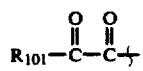

wherein n is 0, 1, 2 and 3; $R_{90}$ is selected from the group consisting of amino, acylamino, hydroxyl, a carboxyl salt, protected carboxy, azido and a sulfo salt; and $R_{101}$ is a substituted or unsubstituted 5-, 6-, or 7-membered heterocyclic ring containing 1, 2, 3 or 4 hetero atoms selected from the group consisting of nitrogen, oxygen and sulfur, the 5-, 6- or 7-membered heterocyclic ring being substituted with halogen, hydroxyl, nitro, amino, cyano, trifluoromethyl, alkyl of 1 to 4 carbon atoms or alkoxy of 1 to 4 carbon atoms.

11. A compound as in claim 1 wherein acyl group $R_3$ is a [[(4-substituted-2,3-dioxo-1-piperazinyl)carbonyl]amino]acetyl group of the formula

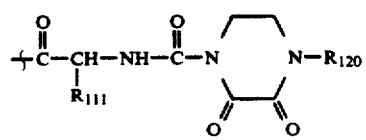

wherein $R_{111}$ is alkyl, hydroxyalkyl or an aromatic group of the formula

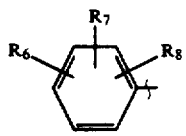

wherein $R_6$, $R_7$, and $R_8$ are independently selected from the group consisting of hydrogen, halogen, hydroxyl, nitro, amino, cyano, trifluoromethyl, alkyl of 1 to 4 carbon atoms, alkoxy of 1 to 4 carbon atoms, aminomethyl, or a substituted or unsubstituted 5-, 6- or 7-membered heterocyclic ring containing 1, 2, 3 or 4 hetero atoms selected from the group consisting of nitrogen, oxygen and sulfur, the 5-, 60 or 7-membered heterocyclic ring being substituted with halogen, hydroxyl, nitro, amino, cyano, trifluoromethyl, alkyl to 1 to 4 carbon atoms or alkoxy of 1 to 4 carbon atoms and $R_{120}$ is alkyl or substituted alkyl, the substituted alkyl group being substituted with one or more halogen, cyano, nitro, amino or mercapto groups.

12. A compound as in claim 1 wherein acyl group $R_3$ is an (acylamino) acetyl group of the formula

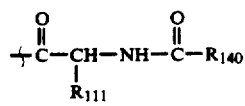

wherein $R_{111}$ is alkyl, hydroxyalkyl or an aromatic group of the formula

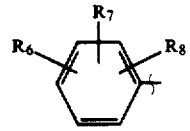

wherein $R_6$, $R_7$ and $R_8$ are independently selected from the group consisting of hydrogen, halogen, hydroxyl, nitro, amino, cyano, trifluoromethyl, alkyl of 1 to 4 carbon atoms, alkoxy of 1 to 4 carbon atoms and aminomethyl, or a substituted or unsubstituted 5-, 6- or 7-membered heterocyclic ring containing 1, 2, 3 or 4 hetero atoms selected from the group consisting of nitrogen, oxygen and sulfur, the 5-, 6- or 7-membered heterocyclic ring being substituted with halogen, hydroxyl, nitro, amino, cyano, trifluoromethyl, alkyl of 1 to 4 carbon atoms or alkoxy of 1 to 4 carbon atoms, and $R_{140}$ is

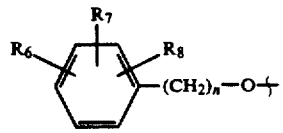

(where $R_6$, $R_7$ and $R_8$ are as previously defined and n is 0, 1, 2 or 3), hydrogen, lower alkyl, lower alkyl substituted with halo, trifluoromethyl, amino and cyano, amino, alkylamino, dialkylamino (cyanoalkyl) amino, hydrazino, alkyl hydroazino, and hydrazino or acyl hydrazino.

13. A compound as in claim 1 wherein acyl group $R_3$ is a (substituted oxyimino) acetyl group having the formula

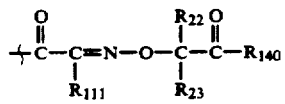

wherein $R_{111}$ is alkyl, hydroxyalkyl or an aromatic group of the formula

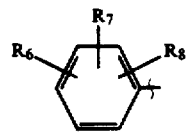

wherein $R_6$, $R_7$ and $R_8$ are independently selected from the group consisting of hydrogen, halogen, hydroxyl, nitro, amino, cyano, trifluoromethyl, alkyl of 1 to 4 carbon atoms, alkoxy of 1 to 4 carbon atoms, and aminomethyl, or a substituted or unsubstituted 5-, 6- or 7-membered heterocyclic ring containing 1, 2, 3 or 4 hetero atoms selected from the group consisting of nitrogen, oxygen and sulfur, the 5-, 6- or 7-membered heterocyclic ring being substituted with halogen, hydroxyl, nitro, amino, cyano, trifluoromethyl, alkyl of 1 to 4 carbon atoms or alkoxy of 1 to 4 carbon atoms, and $R_{140}$ is

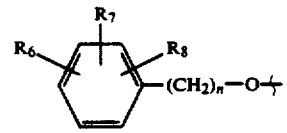

(wherein $R_6$, $R_7$ and $R_8$ are as defined above and n is 0, 1, 2 or 3), hydrogen, lower alkyl, lower alkyl substituted with halo, trifluoromethyl, amino and cyano, amino, alkylamino, dialkylamino, (cycanoalkyl) amino, hydrazino, alkyl hydrazino, aryl hydrazino and acyl hydrazino, and $R_{22}$ and $R_{23}$ are independently selected from the group consisting of hydrogen and lower alkyl, or $R_{22}$ and $R_{23}$ taken together with the carbon atom to which they are attached form a $C_3$–$C_7$ carboxylic ring.

14. A compound as in claim 1 wherein acyl group $R_3$ is a [[[3-substituted-2-oxo-1-imidazolidinyl]-carbonyl-]amino]acetyl group of the formula

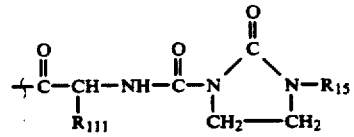

wherein $R_{111}$ is alkyl, hydroxyalkyl or an aromatic group of the formula

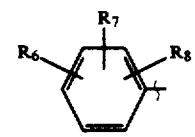

wherein $R_6$, $R_7$ and $R_8$ are independently selected from the group consisting of hydrogen, halogen, hydroxyl, nitro, amino, cyano, trifluoromethyl, alkyl of 1 to 4 carbon atoms, alkoxy of 1 to 4 carbon atoms, aminomethyl, or a substituted or unsubstituted 5-, 6- or 7-membered heterocyclic ring containing 1, 2, 3 or 4 hetero atoms selected from the group consisting of nitrogen, oxygen and sulfur, the 5-, 6- or 7-membered heterocyclic ring being substituted with halogen, hydroxyl, nitro, amino, cyano, trifluoromethyl, alkyl of 1 to 4 carbon atoms or alkoxy of 1 to 4 carbon atoms, and $R_{15}$ is hydrogen, alkylsulfonyl, arylmethyleneamino (i.e., $-N=CHR_{111}$ wherein $R_{111}$ is as defined above),

(wherein $R_{16}$ is hydrogen, alkyl or halogen alkyl substituted with halo, trifluoromethyl, amino and cyano,), aromatic group (as defined by $R_{111}$ above), alkyl or substituted alkyl the substituted alkyl group being substituted with one or more halogen, cyano, nitro, amino or mercapto groups.

15. A compound as in claim 1 wherein acyl group $R_3$ is of the formula

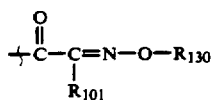

wherein $R_{101}$ is an unsubstituted or substituted 5, 6- or 7-membered heterocyclic ring containing 1, 2, 3 or 4 hereto atoms selected from the group consisting of nitrogen, oxygen and sulfur wherein the heterocyclic ring is substituted by halogen, hydroxy, nitro, amino, cyano, trifluoromethyl, $C_1$ to $C_4$ alkyl or $C_1$ to $C_4$ alkoxy and $R_{130}$ is hydrogen, lower alkyl, $C_3-C_7$ cycloalkyl and substituted lower alkyl wherein the lower alkyl is substituted with one or more halogen, cyano, nitro, amino, mercapto, lower alkylthio, carboxyl (including salts thereof), amido, carbamoyl, lower alkoxycarbonyl, phenylmethoxycarbonyl, diphenylmethoxycarbonyl, hydroxyalkoxyphoephinyl, dihydroxyphoephinyl, hydroxy(phenylmethoxy)phosphinyl, diloweralkoxyphoephinyl carboxyl lower alkyl or carboxyl-3,7-cycloalkyl.

16. A compound as in claim 15 wherein $R_{101}$ is of the formula

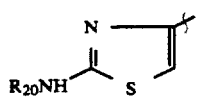

wherein $R_{20}$ is hydrogen or an amino protecting group, and $R_{130}$ is hydrogen, lower alkyl or a group of the formula

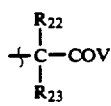

wherein $R_{22}$ and $R_{23}$ are selected from the group consisting of hydrogen and lower alkyl or taken together with the carbon atom to which they are attached form a $C_3-C_7$ carboxylic ring, and y is hydroxy or $NHR_{19}$ where $R_{19}$ is hydrogen, lower alkyl, amino, alkyl amino, aryl amino or acyl amino.

17. A compound as in claim 16 wherein $R_{20}$ is hydrogen or triphenylmethyl.

18. A compound of claim 1, having the formula

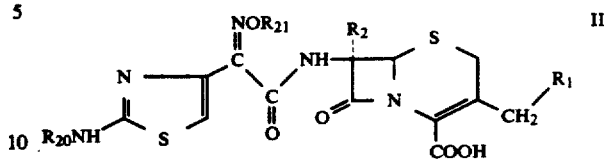

wherein $R_1$ is substituted piperazinium group of the formula

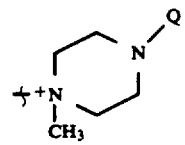

in which Q represents a substituted quinolonyl or naphthyridonyl group and the piperazine nucleus may be unsubstituted or substituted with one or more lower alkyl groups; $R_2$ is selected from the group consisting of hydrogen, lower alkoxy, lower alkylthio and amido; $R_3$ is hydrogen or an acyl group; $R_{20}$ is hydrogen or an amino-protecting group; $R_{21}$ is hydrogen, lower alkyl or a group of the formula

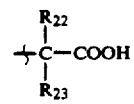

in which $R_{22}$ and $R_{23}$ are independently hydrogen or lower alkyl, or when taken together with the carbon atom to which they are attached form a $C_3-C_7$ carboxylic ring.

19. A compound of claim 1, having the formula

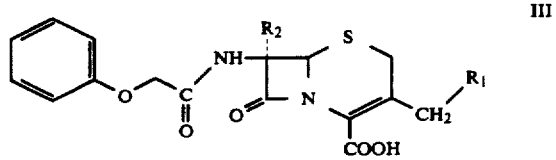

wherein $R_1$ is a piperazinium group of the formula

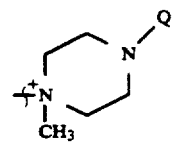

in which Q represents a substituted quinolonyl or naphthyridonyl group and the piperazine nucleus may be unsubstituted or substituted with one or more lower alkyl groups; and $R_2$ is selected from the group consisting of hydrogen, lower alkoxy, lower alkylthio and amido.

20. A compound as in claim 1 of the formula [6R-(6α,7β)]-4-[3-carboxy-1-(2-fluoroethyl)-6,8-difluoro-1,4-dihydro-4-oxoquinolin-7-yl]-[[2-carboxy-8-oxo-7-

[(phenoxyacetyl)amino]-5-thia-1-azabicyclo[4.2.0]oct-2-en-3-yl]methyl]-1-methylpiperazinium iodide.

21. A compound as in claim 1 of the formula (6R-trans)-4-[3-carboxy-1-(2-fluoroethyl)-6,8-difluoro-1,4-dihydro-4-oxoquinolin-7-yl]-1-[[2-carboxy-8-oxo-7-[(phenoxyacetyl)amino]-5-thia-1-azabicyclo-[4.2.0]oct-2-en-3-yl]methyl]-1-methylpiperazinium hydroxide inner salt monosodium salt.

22. A compound as in claim 1 of the formula [6R-[6α,7β(Z)]]-1-[[7-[[[(2-amino-4-thiazolyl)[1-(1-carboxy-1-methyl)ethoxy]imino]acetyl]amino]-8-oxo-5-thia-1-azabicyclo[4.2.0]oct-2-en-3-yl]methyl]-4-[3-carboxy-1-(2-fluoroethyl)-6,8-difluoro-1,4-dihydro-4-oxoquinolin-7-yl]-1-methylpiperazinium hydroxide inner salt monosodium salt.

23. A compound as in claim 1 of the formula [6R-[6α,7β(Z)]]-1-[[7-[[(2-amino-4-thiazolyl)(methoxyimino)acetyl]amino]-2-carboxy-e-oxo-5-thia-1-azabicyclo-[4.2.0]oct-2-en-3-yl]methyl]-4-(3-carboxy-1-ethyl-6-fluoro-1,4-dihydro-4-oxo-7-quinolinyl)-1-methylpiperazinium iodide.

24. A compound as in claim 1 of the formula [6R-[6α,7β(Z)]]-1-[[7-[[[(2-amino-4-thiazolyl)(methoxyimino)acetyl]amino]-2-carboxy-8-oxo-8-thia-1-azabicyclo[4.2.0]oct-2-en-3-yl]methyl]-4-(3-carboxy-1-ethyl-6-fluoro-1,4-dihydro-4-oxo-7-quinolinyl)-1-methyl-piperazinium monosodium salt.

25. A compound as in claim 1 of the formula [6R-[6α,7β(Z)]]-1-[7-[[[(2-amino-4-thiazolyl)(methoxyimino)acetyl]amino]-2-carboxy-8-oxo-5-thia-1-azabicyclo-[4.2.0]oct-2-en-3-yl]methyl]-4-[3-carboxy-6,8-difluoro-1-(2-fluoroethyl)-1,4-dihydro-4-oxo-7-quinolinyl]-1-methyl-piperazinium iodide.

26. A compound as in claim 1 of the formula [6R-[6α,7β(Z)]]-1-[7-[[[(2-amino-4-thiazolyl)(methoxyimino)acetyl]amino]-2-carboxy-8-oxo-5-thia-1-azabicyclo-[4.2.0]oct-2-en-3-yl]methyl]-4-[3-carboxy-6,S-difluoro-1-(2-fluoroethyl)-1,4-dihydro-4-oxo-7-quinolinyl]-1-methyl-piperazinium monosodium salt.

27. A compound as in claim 1 of the formula (6R-trans)-4-[3-carboxy-6,8-difluoro-1-(2-fluoroethyl)-1,4-dihydro-4-oxo-7-quinolinyl]-1-[[2-(1,1-dimethylethoxy)carbonyl-7-(formylamino)-8-oxo-5-thia-1-azabicyclo[4.2.0]oct-2-en-3-yl]methyl]-1-methylpiperazinium iodide.

28. A compound as in claim 1 of the formula (6R-trans)-4-[3-carboxy-6,8-difluoro-1-(2-fluoroethyl)-1,4-dihydro-4-oxo-7-quinolinyl]-1-[[2-carboxy-7-(formylamino)-8-oxo-5-thia-1-azabicyclo[4.2.0]oct-2-en-3-yl]methyl]-1-methylpiperazinium trifluoroacetate salt.

29. A compound ae in claim 1 of the formula [6R-[6α,7β(Z)]]-1-[[7-[[[(2-amino-4-thiazolyl)[[1,1-dimethyl-2-(1,1-dimethylethoxy)-2-oxoethoxy]imino]acetyl]amino]-8-oxo-5-thia-1-azabicyclo[4.2.0]oct-2-en-3-yl]methyl]-4-f3-carboxy-(2-fluoroethyl)-6,8-difluoro-1,4-dihydro-4-oxoquinolin-7-yl]-1-methylpiperazinium iodide.

* * * * *

UNITED STATES PATENT AND TRADEMARK OFFICE
CERTIFICATE OF CORRECTION

PATENT NO. : 5,329,002

DATED : July 12, 1994

INVENTOR(S) : Albrecht, et al.

It is certified that error appears in the above-identified patent and that said Letters Patent is hereby corrected as shown below:

In claim 1, column 23, lines 39-45, delete the chemical formula and insert therefor -- 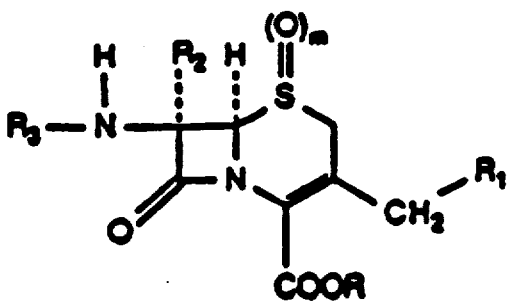    I  --.

In claim 3, column 24, line 32, delete "a" and insert -- an --.

In claim 3, column 24, line 41, delete "-OCH$_2$,".

In claim 3, column 24, line 42, delete "N(CH$_3$)-," and insert therefor -- -OCH$_2$N(CH$_3$)- --.

In claim 11, column 27, line 16, delete "60" and insert therefor -- 6- --.

UNITED STATES PATENT AND TRADEMARK OFFICE
CERTIFICATE OF CORRECTION

PATENT NO. :     5,329,002                    Page 2 of 5
DATED :          July 12, 1994
INVENTOR(S) :    Albrecht, et al.

It is certified that error appears in the above-identified patent and that said Letters Patent is hereby corrected as shown below:

In claim 11, column 27, line 18, delete "to" and insert therefor -- of --.

In claim 12, column 27, line 64, delete "hydroazino, and" and insert therefor -- hydrazino, aryl --.

In claim 13, column 28, line 39, delete "(cycanoalkyl)" and insert therefor -- (cyanoalkyl) --.

In claim 15, column 29, line 29, delete "$R_{101}$is" and insert therefor -- $R_{101}$ is --.

In claim 15, column 29, line 29, delete "5" and insert therefor -- 5- --.

UNITED STATES PATENT AND TRADEMARK OFFICE
CERTIFICATE OF CORRECTION

PATENT NO. : 5,329,002
DATED : July 12, 1994
INVENTOR(S) : Albrecht, et al.

It is certified that error appears in the above-identified patent and that said Letters Patent is hereby corrected as shown below:

In claim 15, column 29, line 31, delete "hereto" and insert therefor -- hetero --.

In claim 15, column 29, line 38, delete "halogen." and insert therefor -- halogen, --.

In claim 15, column 29, line 42, delete "hydroxyalkoxyphoephinyl, dihydroxyphoephinyl" and insert therefor -- hydroxyalkoxyphosphinyl, dihydroxyphosphinyl --.

In claim 15, column 29, line 43, delete "diloweralkoxyphoe-" and insert therefor -- diloweralkoxyphos- --.

In claim 16, column 29, line 66, delete "y" and insert therefor -- V --.

UNITED STATES PATENT AND TRADEMARK OFFICE
CERTIFICATE OF CORRECTION

PATENT NO. : 5,329,002
DATED : July 12, 1994
INVENTOR(S) : Albrecht, et al.

It is certified that error appears in the above-identified patent and that said Letters Patent is hereby corrected as shown below:

In claim 18, column 30, line 12, between "is" and "substituted", insert -- a --.

In claim 23, column 31, line 18, delete "carboxy-e-" and insert therefor -- carboxy-8- --.

In claim 24, column 31, line 24, delete "-8-oxo-8-" and insert therefor -- -8-oxo-5- --.

In claim 25, column 32, line 3, delete "-1.4" and insert therefor -- -1,4 --.

In claim 26, column 32, line 8, delete "6,S-" and insert therefor -- 6,8- --.

UNITED STATES PATENT AND TRADEMARK OFFICE
CERTIFICATE OF CORRECTION

PATENT NO. : 5,329,002
DATED : July 12, 1994
INVENTOR(S) : Albrecht, et al.

It is certified that error appears in the above-identified patent and that said Letters Patent is hereby corrected as shown below:

In claim 29, column 32, line 22, delete "ae" and insert therefor -- as --.

In claim 29, column 32, line 23, after "[[1,1-di", insert -- - --.

In claim 29, column 32, line 26, delete "4-f3-" and insert therefor -- 4-[3- --.

Signed and Sealed this

Sixteenth Day of May, 1995

Attest:

BRUCE LEHMAN

Attesting Officer     Commissioner of Patents and Trademarks